United States Patent
Groot et al.

(10) Patent No.: US 9,162,961 B2
(45) Date of Patent: Oct. 20, 2015

(54) PROCESS FOR MANUFACTURING SUCCINIC ACID

(75) Inventors: Willem Jacob Groot, Dordrecht (NL); Jan Van Breugel, Woudrichem (NL)

(73) Assignee: Purac Biochem BV, Gorinchem (NL)

( * ) Notice: Subject to any disclaimer, the term of this patent is extended or adjusted under 35 U.S.C. 154(b) by 277 days.

(21) Appl. No.: 13/578,350

(22) PCT Filed: Feb. 14, 2011

(86) PCT No.: PCT/EP2011/052128
§ 371 (c)(1),
(2), (4) Date: Aug. 10, 2012

(87) PCT Pub. No.: WO2011/098598
PCT Pub. Date: Aug. 18, 2011

(65) Prior Publication Data
US 2012/0316368 A1  Dec. 13, 2012

Related U.S. Application Data

(60) Provisional application No. 61/303,767, filed on Feb. 12, 2010.

(30) Foreign Application Priority Data
Feb. 12, 2010 (EP) .................... 10153437

(51) Int. Cl.
| | | |
|---|---|---|
| *C25B 7/00* | (2006.01) | |
| *C07C 27/06* | (2006.01) | |
| *C07C 51/41* | (2006.01) | |
| *C07C 29/149* | (2006.01) | |
| *C07C 51/02* | (2006.01) | |
| *C07C 51/43* | (2006.01) | |
| *C12P 7/46* | (2006.01) | |

(52) U.S. Cl.
CPC .............. *C07C 51/412* (2013.01); *C07C 29/149* (2013.01); *C07C 51/02* (2013.01); *C07C 51/43* (2013.01); *C12P 7/46* (2013.01)

(58) Field of Classification Search
None
See application file for complete search history.

(56) References Cited

U.S. PATENT DOCUMENTS

| | | |
|---|---|---|
| 5,034,105 A | 7/1991 | Berglund |
| 5,143,834 A | 9/1992 | Glassner |
| 2004/0039213 A1 | 2/2004 | Hepfer |
| 2006/0004212 A1 | 1/2006 | Bhattacharyya et al. |
| 2007/0015264 A1 | 1/2007 | Isotani |

FOREIGN PATENT DOCUMENTS

| | | |
|---|---|---|
| EP | 0389103 | 9/1990 |
| EP | 1686183 | 8/2006 |
| EP | 1686183 A1 * | 8/2006 |
| EP | 2157185 | 2/2010 |
| WO | WO 02/18316 | 3/2002 |
| WO | WO02/18316 A2 * | 3/2002 |

OTHER PUBLICATIONS

First Office Action issued by the State Intellectual Property Office of the People's Republic of China on Jan. 17, 2014, in corresponding Chinese Patent Application No. 201180008775.8 (2 pages).
European Search Report and Written Opinion of the European Patent Office Patent Office in counterpart foreign application No. PCT/EP2011/052128 filed Feb. 14, 2011.

* cited by examiner

*Primary Examiner* — Christian Fronda
(74) *Attorney, Agent, or Firm* — Peter J. Ims; Westman, Champlin & Koehler, P.A.

(57) ABSTRACT

A process for the preparation of succinic acid comprising the steps of:
a) providing an aqueous medium comprising magnesium succinate by fermentation of a carbohydrate source, in the presence of a magnesium base;
b) processing the aqueous medium wherein the magnesium succinate is treated with a monovalent base, prior to or after a crystallization step, to provide a magnesium base and an aqueous solution comprising a monovalent succinate salt;
c) adjusting the concentration of the monovalent succinate salt to between 10 and 35 wt. %;
d) subjecting the aqueous solution to water-splitting electrodialysis, to produce a first solution comprising monovalent base and a second solution comprising succinic acid and monovalent succinate salt, the electrodialysis causing conversion of 40 to 95 mole %;
e) separating the second solution into succinic acid and the monovalent succinate salt by crystallization;
f) recycling the monovalent succinate salt solution of step e) to step d).

20 Claims, No Drawings

PROCESS FOR MANUFACTURING SUCCINIC ACID

CROSS-REFERENCE TO RELATED APPLICATION

This application is a Section 371 National Stage Application of International Application No. PCT/EP2011/052128, filed Feb. 14, 2011 and published as WO 2011/098598 on Aug. 18, 2011, in English, which in turn is based on and claims benefit of U.S. Provisional Application No. 61/303,767, filed Feb. 12, 2010.

BACKGROUND

The discussion below is merely provided for general background information and is not intended to be used as an aid in determining the scope of the claimed subject matter.

An aspect of the present invention pertains to a process for manufacturing succinic acid in high purity in an economical manner.

Succinic acid is often manufactured via fermentation of carbohydrates by micro-organisms. A common feature to all fermentation processes is the need to neutralise the acids excreted by the micro-organisms. A drop in pH below a critical value, depending on the micro-organism used in the process, could damage the microorganism's metabolic process and bring the fermentation process to a stop. Therefore, it is common practice to add a base in the fermentation media in order to control the pH. This results in the succinic acid produced being present in the fermentation media in the form of a succinate salt.

Despite the longstanding practice to produce succinic acid via fermentation, one of the challenges in the manufacture of succinic acid is still to obtain the acid in a relatively pure form while at the same time carrying out the process in an economical manner on a scale which is commercially attractive.

Electrodialysis is one of the purification processes that may be used in the production of succinic acid via fermentation. Water-splitting electrodialysis in particular allows the direct conversion of the succinate salt into succinic acid and base. In this type of electrodialysis bipolar membranes are generally used to split water into $H^+$ and $OH^-$ respectively, which combine with the anion and cation of the succinate salt respectively, resulting in the production of separate solutions of succinic acid and base.

There is still need for a process for manufacturing succinic acid which provides succinic acid in high purity and which can be performed in an economical manner with a low power consumption, without producing substantial amounts of non-reusable components (i.e. waste by-products) and without substantial yield loss.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background. An aspect of the present disclosure includes a process where magnesium succinate is provided by fermentation and treated by means of crystallisation and salt exchange to provide an aqueous solution of a monovalent succinate salt which is especially suited for subsequent water-splitting electrodialysis. Succinic acid of high purity is produced by using water-splitting electrodialysis with a partial conversion of the succinate salt to succinic acid, separating the succinic acid from the succinate salt by crystallisation and recycling the succinate salt to the electrodialysis process.

DETAILED DESCRIPTION

It has been found that the process for the manufacture of succinic acid as described herein is very efficient and economical, provides high production yields, minimal product losses and results in succinic acid of high quality.

Accordingly, an aspect of the present invention pertains to a process for the preparation of succinic acid comprising the steps of:

a) providing an aqueous medium comprising magnesium succinate by fermentation, wherein a carbohydrate source is fermented by means of a microorganism to form succinic acid, a magnesium base being added as neutralising agent during fermentation to provide the magnesium succinate;

b) subjecting the aqueous medium comprising magnesium succinate to a crystallisation step and a salt exchange step to provide an aqueous solution comprising a monovalent succinate salt, wherein the salt exchange, which is performed either prior to or after crystallisation, comprises treating the magnesium succinate with a monovalent base to provide a magnesium base and the monovalent succinate salt;

c) adjusting the concentration of the monovalent succinate salt in the aqueous solution to a value between 10 and 35 wt. %;

d) subjecting the aqueous solution comprising the monovalent succinate salt to water-splitting electrodialysis, to produce a first solution comprising monovalent base and a second solution comprising succinic acid and monovalent succinate salt, the electrodialysis being carried out to a partial conversion of 40 to 95 mole %;

e) separating the second solution comprising succinic acid and monovalent succinate salt into succinic acid and a solution comprising the monovalent succinate salt by crystallisation;

f) recycling the solution of step e) comprising the monovalent succinate salt to step d).

The use of magnesium base during the fermentation step a) advantageously results in the formation of magnesium succinate, which is soluble in the fermentation broth. The inventors have found that a separate and controlled crystallisation can be performed from a fermentation broth neutralised with magnesium base. This is not the case when using other bases such as a calcium base. The use of calcium base generates calcium succinate, which tends to crystallise during fermentation in a less controlled manner than magnesium succinate. In addition, the calcium succinate crystals obtained tend to be more difficult to separate from the fermentation broth.

As a result of the crystallisation and salt exchange steps performed on the magnesium succinate obtained via fermentation, the aqueous solution comprising monovalent succinate salt provided in step b) is of such quality that it may be directly subjected to water-splitting electrodialysis to provide succinic acid.

Carrying out the water-splitting electrodialysis to a partial conversion of 40 to 95 mole % and subsequently recycling the remaining succinate salt to the electrodialysis step advantageously results in an optimal process with low power consumption and no substantial yield loss.

Furthermore, the process as described herein produces virtually no waste by-products, since all compounds formed and separated in the different steps may be recycled. The magnesium base of step b) may for instance be used in the fermentation step a) and the solution comprising monovalent base of step d) may be used in the salt exchange of step b). The separation step e) also contributes to minimise the amount of non-reusable components since it does not generate further waste by-products.

The aqueous medium comprising magnesium succinate is provided by a fermentation process. The magnesium succinate salt is generally already present in an aqueous medium when it leaves the fermentation. In such a process, a carbohydrate source is fermented to succinic acid by means of a succinic acid-producing micro-organism. During fermentation, a magnesium base is added as neutralising agent. This results in the formation of an aqueous medium comprising the corresponding magnesium succinate salt.

The base anion of the magnesium base is preferably chosen from at least one of hydroxide, carbonate and hydrogencarbonate, and more preferably is hydroxide. Although the use of magnesium as the base cation is preferred, another alkaline earth metal cation, such as a calcium cation, may also be used. The amount of alkaline earth metal base added is determined by the amount of succinic acid produced and may be determined via pH control of the fermentation medium.

The biomass (i.e. microbial cell matter) may be removed from the fermentation broth before further processing of the succinate-containing medium. Biomass removal may be effected, for example, by conventional methods including filtration, flotation, sedimentation, centrifugation, flocculation and combinations thereof. It is within the skills of the skilled person to determine an appropriate method. Other optional treatments prior to further processing include washing, filtration, (re)crystallisation, concentration and combinations thereof.

The aqueous medium comprising the alkaline earth metal succinate salt, preferably magnesium succinate, is subjected to a crystallisation step and a salt exchange step to provide an aqueous solution comprising a monovalent succinate salt. The monovalent succinate salt obtained is especially suitable for water-splitting electrodialysis since it is substantially free of fermentation-derived products (e.g. sugar, protein, amino acids) which may negatively interfere in water-splitting electrodialysis by, for instance, increasing the power consumption and fouling of the ion-permeable membranes.

The salt exchange step, which may be performed either prior to or after crystallisation, comprises treating the alkaline earth metal succinate salt with a monovalent base to provide an alkaline earth metal base and the monovalent succinate salt.

The monovalent base used in the salt exchange is preferably a hydroxide, carbonate and/or hydrogencarbonate, more preferably a hydroxide, of a monovalent cation, the monovalent cation being sodium, potassium, lithium, ammonium, monoalkylammonium, dialkylammonium, trialkylammonium or tetraalkylammonium, preferably sodium or potassium and more preferably sodium. Generally, the use of sodium and potassium bases advantageously results in a higher conversion of the alkaline metal earth succinate salt to the monovalent succinate salt than when ammonium bases are used. This is relevant for preparing a product with a low alkaline earth metal ion content suitable for water-splitting electrodialysis. The base anion is generally chosen to correspond to the base anion used as neutralising agent during fermentation.

The amount of monovalent base is determined by stoichiometric and pH considerations. It may be preferred to use a surplus of base to obtain a high conversion and to ensure the removal of virtually all alkaline earth metal ions from the succinate.

The alkaline earth metal base obtained as a result of the salt exchange of step b) may be recycled to the fermentation step a).

The crystallisation may comprise at least one of a concentration step, such as a water evaporation step, a cooling step, a seeding step, a separation step, a washing step and a re-crystallisation step. Concentration may be performed as a separate step or together with crystallisation (e.g. evaporative-crystallisation).

When crystallisation is performed prior to salt exchange, the alkaline earth metal succinate salt is crystallised from the aqueous medium provided by fermentation by concentrating the fermentation broth (e.g. by evaporation of water), preferably after biomass removal. The alkaline earth metal succinate crystals obtained are then separated from the liquid phase, which contains the fermentation-derived products, providing a purified alkaline earth metal succinate salt. The salt exchange may then be performed in batch or in continuous mode. In batch mode, an aqueous solution comprising a monovalent base is slowly added to a solution or slurry containing the alkaline earth metal succinate salt. The alkaline earth metal base formed in the salt exchange step typically is in solid form while the monovalent succinate salt is dissolved in the aqueous phase. The salt exchange may preferably be performed in continuous mode. When the salt exchange is performed in continuous mode, a slurry of the alkaline earth metal succinate salt crystals (e.g. magnesium succinate) and an aqueous solution of the monovalent base (e.g. sodium hydroxide) are mixed in a reactor to generate a slurry comprising the alkaline earth metal base in solid form (e.g. magnesium hydroxide) and the monovalent succinate salt dissolved in the aqueous phase (e.g. sodium succinate). The two resulting components may be separated by conventional solid-liquid separation processes, such as filtration and/or sedimentation, providing the aqueous solution comprising the monovalent succinate salt.

When the salt exchange is performed prior to crystallisation, the monovalent base is added to the aqueous medium comprising the alkaline earth metal succinate salt provided by fermentation, preferably after biomass removal. As discussed above, the solid alkaline earth metal base formed may be separated from the aqueous medium comprising the aqueous soluble monovalent succinate salt. The monovalent succinate salt is then crystallised from the aqueous medium by concentrating the aqueous medium (e.g. by evaporation of water) and the crystals are separated from the liquid phase, which contains the fermentation-derived products, providing a purified monovalent succinate salt. The aqueous solution comprising the monovalent succinate salt may be obtained by for example dissolving the separated succinate crystals in water.

The aqueous solution of monovalent succinate salt may be subjected to additional treatments prior to water-splitting electrodialysis, such as ion exchange treatment, activated carbon treatment, desalting electrodialysis, dilution, concentration and/or filtration (e.g. nanofiltration). For instance, as a safety measure to prevent a too high alkaline earth metal level in the aqueous solution comprising the monovalent succinate salt, an ion exchange step may be performed prior to electrodialysis to lower the alkaline earth metal content thereof.

However, the process as described herein advantageously does not necessitate such additional treatments, especially when a magnesium base is added in the fermentation process to provide a magnesium succinate fermentation broth.

The aqueous solution comprising the monovalent succinate salt is then subjected to water-splitting electrodialysis.

The initial concentration of the monovalent succinate salt in the aqueous solution that is subjected to electrodialysis (the feed solution) is between 10 and 35 wt. %. Preferably, the monovalent succinate salt concentration is between 20 and 35 wt. %, more preferably between 20 and 30 wt. % and most preferably between 22 and 28 wt. %. Depending on the salt concentration, the aqueous solution comprising the monovalent succinate salt may be used directly after step b), or, if necessary, may be diluted or concentrated to adjust the salt concentration prior to water-splitting electrodialysis. Concentration may be carried out by for instance evaporation or desalting electrodialysis.

The concentration of the monovalent succinate salt in the aqueous medium may be determined by methods known to the skilled person, for instance by using conductivity measurements or Inductively Coupled Plasma mass spectrometry analysis.

The water-splitting electrodialysis is carried out to a partial conversion of 40 to 95 mole %. Preferably, the electrodialysis is carried out to a conversion of 50 to 95 mole %, more preferably of 60 to 95 mole %, even more preferably of 70 to 90 mole %, even more preferably of 80 to 90 mole %, and most preferably of 85 mole %. A first solution comprising monovalent base and a second solution comprising succinic acid and monovalent succinate salt are produced in this process.

A partial conversion of 40 to 95 mole % means that 40 to 95 mole % of the monovalent succinate salt is converted into succinic acid. This results in the second solution produced by the electrodialysis comprising succinic acid in an amount of 40 to 95 mole %, calculated on the total molar amount of succinic acid and succinate present in the solution.

The degree of conversion may be monitored by measuring conductivity of the second solution using methods known to the person skilled in the art.

In addition to the conversion level and the initial salt concentration of the feed solution, the conductivity of the second solution will depend on the temperature of the electrodialysis process. The higher the temperature at which the electrodialysis is performed, the lower the power consumption will be. Hence, the working temperature is chosen to optimise power consumption without compromising the performance and the life of the ion-specific permeable membranes. Generally, the water-splitting electrodialysis is performed at a temperature between 25° C. and 40° C. However, it is preferred to conduct the electrodialysis at a temperature higher than 50° C., for instance between 60° C. and 80° C., to allow for a low power consumption and the possibility for heat recovery.

Because of the limited solubility of succinic acid in water, in order to avoid crystallisation of succinic acid during water-splitting electrodialysis, the working conditions of the electrodialysis are chosen to ensure that the concentration of succinic acid in the final solution is below saturation. For instance, for a conversion of 40 to 95 mole % and a working temperature of 25° C., at which the solubility of succinic acid in water is about 8 wt. %, the initial sodium succinate concentration should be between 10 and 25 wt. %. When working at higher temperatures, the concentration of sodium succinate in the feed solution may be higher.

The water-splitting electrodialysis as described herein may be performed using a conventional apparatus and conventional methods. Preferably the water-splitting electrodialysis is carried out in an electrodialysis apparatus provided with a cation exchange membrane and a bipolar membrane. A typical water-splitting electrodialysis cell comprises a series of a two compartment unit, generally a series of about 50 units. The aqueous medium comprising the monovalent succinate salt is introduced in the salt/acid compartment (or feed compartment). The monovalent cations are transported from the salt/acid compartment to the base compartment through the cation exchange membrane to produce the first solution comprising the monovalent base. Simultaneously, $H^+$ ions are transported to the salt/acid compartment to produce the second solution comprising succinic acid and monovalent succinate salt.

It is preferred to apply the water-splitting electrodialysis to monovalent succinate salts of sodium and potassium. When using ammonium succinate, care must be taken to control the emission of toxic ammonia resulting from the generation of ammonium hydroxide.

The second solution produced by the water-splitting electrodialysis is separated into succinic acid and a solution comprising the monovalent succinate salt by crystallisation.

The succinic acid may be crystallised in a static crystallisation unit, by fractional crystallisation, by suspension crystallisation and/or by wash column crystallisation. The crystallisation may comprise a concentration step, such as a water evaporation step, a cooling step and/or a seeding step and one or more washing steps. The crystals may then be separated from the liquid phase of the solution crystals by filtration or centrifugation.

The solution containing the monovalent succinate salt obtained after separation step e), which may comprise residual succinic acid, is recycled to the water-splitting electrodialysis. This recycling step ensures that no substantial yield loss is suffered as a consequence of the partial conversion of the succinate into succinic acid during water-splitting electrodialysis.

The succinic acid obtained after the separation step e) is generally in solid form (e.g. crystalline) and has a purity of at least 99 wt. %, preferably at least 99.5 wt. %, more preferably at least 99.7 wt. % and most preferably at least 99.9 wt. %.

The succinic acid obtained by the process according to an aspect of the invention is of high purity and is suitable for direct use in numerous applications such as synthetic processes, food applications and cosmetic applications. The succinic acid can be directly used as a monomer in polymerisation processes (e.g. for the formation of polyamides) or as a precursor of other important products and synthetic intermediates such as succinic acid esters, succinic acid anhydride and diamino butane. The succinic acid obtained is particularly suited for the production of butanediol (e.g. by hydrogenation), which is an important intermediary product in polymer production.

The process as described herein advantageously is accompanied by a low power consumption and ensures that no or substantially no waste by-products are generated.

Aspects of the present invention are further illustrated by the following Examples, without being limited thereto or thereby.

Example 1

Crystallisation of Magnesium Succinate

In a jacketed 0.5 L vessel 150.0 g of magnesium succinate tetrahydrate (synthesised from succinic acid 99% from Acros and magnesium oxide 98% from Acros) was suspended in 199.9 g of demineralised water, in order to obtain a magnesium succinate content of 28 wt. % (expressed as anhydrate).

To this mixture 8.1 g of sodium lactate (60%, Purasal S from Purac), as well as 2.6 g of sodium acetate (anhydrous from Fluka) and 10.0 g of yeast extract paste (65% from Bio Springer) were added to simulate a succinic acid fermentation broth and to track the presence of impurities in the final magnesium succinate crystals.

The mixture was heated by means of a thermostatic bath to 90° C., in order to dissolve all solids. After 30 minutes the solution still contained solids. Each 30 minutes some water was added to a total amount of 147.4 g. At this stage all de solids were dissolved and the total volume was about 450 ml.

The mixture was cooled from 90 to 20° C. in 5 hours and allowed to stir during the night. No solids were formed. The mixture was heated again to 80° C. and 100 ml of water was allowed to evaporate.

Then the concentrated solution was cooled from 80° C. to 60° C. in 30 minutes and seed crystals were added. Then the mixture was cooled linearly from 60° C. to 20° C. in 3 hours. During the cooling crystallization nucleation took place at 37° C.

The resulting suspension was separated by means of a filtering centrifuge. After centrifugation an amount of 72.8 g of solid magnesium succinate was obtained.

The samples were analysed on sodium content, lactate and acetate content, total nitrogen content and colour (APHA, a known method for the measurement of colour). The results are shown in Table 1.

TABLE 1

| sample | acetic acid (wt. %) | lactic acid (wt. %) | Na (mg/kg) | total nitrogen (mg/kg) | fresh colour (APHA) |
|---|---|---|---|---|---|
| 1 Crystals | 0.22 | 0.23 | 820 | 390 | 12[1] |
| 2 Mother liquor | 0.69 | 0.68 | 6400 | 3100 | n.a. |

[1]This is the colour of a 10% solution in water at 50° C.

The amount of impurities in the magnesium succinate crystals is significantly reduced compared to the amount of impurities in the mother liquor. In addition, the colour-value measured in the solution of the magnesium succinate crystals indicates that the residual colour in the crystals is very low.

The purity of the magnesium succinate crystals may be improved by washing of the crystals.

Example 2

Salt Exchange of Calcium Succinate and Magnesium Succinate with Monovalent Base

Preparation of Starting Materials:

For preparation of magnesium succinate in an aqueous medium (solution), 80.0 g of succinic acid were dissolved in 1000.0 g of water. After heating to 50° C., a stoichiometric amount of solid magnesium oxide (27.3 g) was added. To make sure all of the succinic acid would react, a small surplus (2.3 g) of MgO was added. Finally, the mixture was filtered over a Büchner funnel, equipped with a filter paper. The filtrate, being a 9.4 wt. % solution of magnesium succinate, was collected. Calcium succinate in an aqueous medium (suspension) was prepared in an analogous manner by letting succinic acid (80.0 g+4.2 g surplus in 1000.1 g water) react with solid calcium hydroxide (50.6 g). After filtration and washing with approximately 800 ml of demineralised water, the residue (calcium succinate) was collected and dried in a desiccation stove for 18 hours at 80° C. The calcium succinate was then suspended in water. The slight surplus of reagents in both reactions was applied in order to obtain succinates with a minimal amount of impurities.

Experiments:

Magnesium succinate and calcium succinate were reacted with various bases to investigate the effectivity of the salt exchange process. The following monovalent bases were used: sodium hydroxide [NaOH], sodium carbonate [$Na_2CO_3$], ammonium carbonate [$(NH_4)_2CO_3$] and ammonium hydroxide [$NH_4OH$].

The reactions were carried out in 500 ml beakers or Erlenmeyer flasks containing 100 ml of 10 wt. % magnesium succinate or calcium succinate in aqueous medium. Sodium carbonate and ammonium carbonate were added in solid form in stoichiometric amounts. Ammonia and NaOH were added in solute form, also in stoichiometric amounts. The reaction mixtures were stirred using a stirring bar and a magnetic stirrer. The amounts of alkaline earth metal succinate and monovalent base used in each reaction are shown in Table 2.

TABLE 2

| Exp. # | Reaction | m(Mg/Ca-Succ.) [g] | Base [g] |
|---|---|---|---|
| 1 | MgSucc + $NH_4OH$ | 99.7 | 9.2 |
| 2 | MgSucc + NaOH | 100.0 | 10.8 (+89.4 $H_2O$) |
| 3 | MgSucc + $Na_2CO_3$ | 99.9 | 7.2 |
| 4 | MgSucc + $(NH_4)_2CO_3$ | 99.6 | 6.5 |
| 5 | CaSucc + $NH_4OH$ | 10.0 + 89.8 $H_2O$ | 8.8 |
| 6 | CaSucc + NaOH | 10.0 + 90.1 $H_2O$ | 10.5 |
| 7 | CaSucc + $Na_2CO_3$ | 10.0 + 90.1 $H_2O$ | 6.8 |
| 8 | CaSucc + $(NH_4)_2CO_3$ | 10.0 + 90.1 $H_2O$ | 6.1 |

The mixtures were allowed to react for 1 hour. From each reaction mixture, samples of 25 ml were taken. These were centrifuged, after which Mg (or Ca) and succinate were determined analytically. The analytical data and the initial concentration of $Mg^{2+}/Ca^{2+}$ or succinate were used for calculation of the conversion of magnesium succinate or calcium succinate to sodium or ammonium succinate. The results are given in Table 3.

TABLE 3

| Experiment | pH | Mg/Ca [ppm] | Succinate [wt. %] | Conversion [%] |
|---|---|---|---|---|
| 1: MgSucc + $NH_4OH$ | 9.6 | 8415 | 6.9 | 43.0 |
| 2: MgSucc + NaOH | 12.4 | 12 | 4.0 | 99.8 |
| 3: MgSucc + $Na_2CO_3$ | 10.5 | 880 | 7.7 | 94.1 |
| 4: MgSucc + $(NH_4)_2CO_3$ | 7.8 | 9487 | 7.5 | 37.4 |
| 5: CaSucc + $NH_4OH$ | 11.1 | 3489 | 1.0 | 12.7 |
| 6: CaSucc + NaOH | 13.0 | 281 | 6.5 | 95.4 |
| 7: CaSucc + $Na_2CO_3$ | 10.5 | 19 | 7.0 | 99.3 |
| 8: CaSucc + $(NH_4)_2CO_3$ | 8.0 | 829 | 7.0 | 98.7 |

As can be seen from Table 3, when sodium hydroxide is used, a conversion of well above 90% is obtained both for magnesium succinate and for calcium succinate. The same applies when sodium carbonate is used. For ammonium carbonate it should be noted that while for calcium succinate a conversion of 98.7% is obtained, the conversion for magnesium succinate is only 37.4%.

Example 3

Partial Electrodialysis of a Sodium Succinate Solution

An Electrocell electrodialysis module (Sweden) was equipped with a Fumatech FBM bipolar membrane, and a Neosepta CMB cation exchange membrane. A set-up with two electrode compartment and one feed compartment was used. The membrane areas of the bipolar and the cation exchange membrane was 0.01 m$^2$. The first compartment comprised of the anode and the cation exchange side of the bipolar membrane, the second feed compartment of the anion exchange side of the bipolar membrane and the cation exchange membrane, and the third compartment of the cation exchange membrane and the cathode. 2 wt. % sulfuric acid in water was circulated through the anode compartment to ensure a high conductivity. A 30.5 wt. % sodium succinate solution was circulated through the middle compartment as a feed. The feed solution was prepared by dissolving 237.6 g sodium succinate in 540.8 g demineralised water. A 6 wt. % sodium hydroxide solution was circulated through the cathode compartment to ensure a high conductivity at the cathode side, and to collect the sodium hydroxide produced. The three solutions were circulated with a peristaltic pump at 250 ml/min from a 500 ml glass buffer over the electrodialysis module. The glass buffer vessels were double walled. The sulphuric acid, sodium hydroxide were reagent grade, and the Purac sodium succinate was of high purity food grade quality.

The temperature across the three compartments was kept between 40 and 60° C. with a water bath. The electrodialysis experiment was carried out a constant 7.5 A DC current. No crystallisation of succinic acid was observed in the electrodyalisis module during the experiment.

During water-splitting electrodialysis the sodium succinate solution in the feed compartment of the module is acidified batch wise through sodium removal through the cation exchange membrane to form sodium hydroxide in the cathode compartment, while protons generated by the bipolar membrane form succinic acid with the original succinate ions.

In the beginning of the experiment the conductivity of the feed (sodium succinate solution) was about 160 mS/cm and the voltage about 10 V. During the first 250 minutes of the experiment the voltage increased slowly to 11 V, coinciding with a conductivity decrease. In the interval between 550 and 626 minutes the voltage had increased from about 12 V to 16 V and the conductivity decreased from about 50 mS/cm to 14.62 mS/cm. At this point the conversion was 95% and the experiment was stopped.

Voltage increase results in a rapid increase in power consumption to convert the residual sodium succinate.

The solution comprising 36.7 wt. % of succinic acid and 2.8 wt. % of sodium succinate was cooled down to room temperature, during which succinic acid crystals formed. The fluid was then poured off and the solid succinic acid was dried in a stove for 15 hours.

Example 4

Crystallisation of Succinic Acid from a Succinic Acid/Sodium Succinate Solution

In a crystalliser (500 ml open jacketed glass vessel) 100.1 g (0.848 mole) of succinic acid (Acros) and 19.9 g (0.074 mole) of sodium succinate hexahydrate (Acros) were dissolved in 281.5 g of demineralised water, by heating with the thermostatic bath to 80° C. This resulted in a clear solution with 25% of succinic acid and 3% of sodium succinate, representing a solution obtained from a water-splitting electrodialysis process with a conversion of 92 mole %. The solution was cooled from 80° C. to 20° C. in 5 hours with a linear cooling profile. During cooling nucleation took place between 56° C. and 50° C.

The resulting crystals were separated by means of a filtering centrifuge. After centrifugation an amount of 70.2 g of solid succinic acid was obtained.

Samples of the motherliquor and the succinic acid crystals were analysed on sodium content, while the motherliquor was also analysed on succinate content. The crystals were analysed without drying.

The sodium content of the crystals was found to be 165 ppm, as compared to 10400 ppm in the mother liquor, whereas the content of succinic acid in the mother liquor was of 12 wt. %.

The amount of sodium was considerably reduced in the crystals when compared to the motherliquor. The amount of sodium in the crystals may be lowered further by washing during centrifugation.

The invention claimed is:

1. A process for the preparation of succinic acid comprising:
    a) providing an aqueous medium comprising magnesium succinate by fermentation, wherein a carbohydrate source is fermented by means of a micro-organism to form succinic acid, a magnesium base being added as neutralising agent during fermentation to provide the magnesium succinate;
    b) subjecting the aqueous medium comprising magnesium succinate to a crystallisation step and a salt exchange step to provide an aqueous solution comprising a monovalent succinate salt, wherein the salt exchange, which is performed either prior to or after crystallisation, comprises treating the magnesium succinate with a monovalent base to provide a magnesium base and the monovalent succinate salt;
    c) adjusting the concentration of the monovalent succinate salt in the aqueous solution to a value between 10 and 35 wt. %;
    d) subjecting the aqueous solution comprising the monovalent succinate salt to water-splitting electrodialysis, to produce a first solution comprising monovalent base and a second solution comprising succinic acid and monovalent succinate salt, the electrodialysis being carried out to a partial conversion of 40 to 95 mole %;
    e) separating the second solution comprising succinic acid and monovalent succinate salt into succinic acid and a solution comprising the monovalent succinate salt by crystallisation;
    f) recycling the solution of step e) comprising the monovalent succinate salt to step d).

2. The process according to claim 1, wherein in step b) the salt exchange is performed after crystallisation.

3. The process according to claim 1, wherein in step c) the concentration of the monovalent succinate salt in the aqueous solution is adjusted to a value between 20 and 35 wt. %.

4. The process according to claim 1, wherein the electrodialysis step d) is carried out to a partial conversion of 50 to 95 mole %.

5. The process according to claim 3, wherein the electrodialysis is carried out to a partial conversion of 85 mole %.

6. The process according to claim 1, wherein the first solution comprising the monovalent base produced by the water-splitting electrodialysis step d) is recycled to step b).

7. The process according to claim 1, wherein the water-splitting electrodialysis is carried out in an electrodialysis apparatus provided with a cation exchange membrane and a bipolar membrane.

8. The process according to claim 1, wherein the magnesium base of step a) is magnesium hydroxide.

9. The process according to claim 1, wherein the aqueous medium comprising the magnesium succinate is subjected to a separation step to remove microbial cell matter prior to step b).

10. The process according to claim 1, wherein the monovalent base in step b) comprises a cation that is a sodium, potassium, lithium, ammonium, monoalkylammonium, dialkylammonium, trialkylammonium or tetraalkylammonium cation.

11. The process according to claim 1, wherein the succinic acid obtained after the separation step e) is in solid form and has a purity of at least 99 wt. %.

12. The process according to claim 1, wherein in step c) the concentration of the monovalent succinate salt in the aqueous solution is adjusted to a value between 20 and 30 wt. %.

13. The process according to claim 1, wherein in step c) the concentration of the monovalent succinate salt in the aqueous solution is adjusted to a value between 22 and 28 wt. %.

14. The process according to claim 1, wherein the electrodialysis step d) is carried out to a partial conversion of 60 to 95 mole %.

15. The process according to claim 1, wherein the electrodialysis step d) is carried out to a partial conversion of 70 to 90 mole %.

16. The process according to claim 1, wherein the electrodialysis step d) is carried out to a partial conversion of 80 to 90 mole %.

17. The process according to claim 1, wherein the succinic acid obtained after the separation step e) is in solid form and has a purity of at least 99.5 wt. %.

18. The process according to claim 1, wherein the succinic acid obtained after the separation step e) is in solid form and has a purity of at least 99.7 wt. %.

19. The process according to claim 1, wherein the succinic acid obtained after the separation step e) is in solid form and has a purity of at least 99.9 wt. %.

20. The process according to claim 1, wherein the monovalent base in step b) comprises a cation that is a sodium or potassium cation.

* * * * *